United States Patent
Matsuzawa (10) Patent No.: US 9,500,524 B2
(45) Date of Patent: Nov. 22, 2016

(54) ICP EMISSION SPECTROMETER

(71) Applicant: Hitachi High-Tech Science Corporation, Minato-ku, Tokyo (JP)

(72) Inventor: Osamu Matsuzawa, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 0 days.

(21) Appl. No.: 14/674,052

(22) Filed: Mar. 31, 2015

(65) Prior Publication Data

US 2015/0276484 A1  Oct. 1, 2015

(30) Foreign Application Priority Data

Mar. 31, 2014 (JP) ................................ 2014-072522

(51) Int. Cl.

| | |
|---|---|
| *G01J 3/30* | (2006.01) |
| *G01J 3/443* | (2006.01) |
| *G01N 21/73* | (2006.01) |
| *G01J 3/06* | (2006.01) |
| *G01N 21/68* | (2006.01) |

(52) U.S. Cl.
CPC .................. *G01J 3/443* (2013.01); *G01J 3/06* (2013.01); *G01N 21/68* (2013.01); *G01N 21/73* (2013.01)

(58) Field of Classification Search
CPC ................................ G01J 3/443; G01N 21/73
USPC .......................................................... 356/316
See application file for complete search history.

(56) References Cited

U.S. PATENT DOCUMENTS

2012/0023456 A1* 1/2012 Sun ....................... G06T 7/0081
715/863

FOREIGN PATENT DOCUMENTS

JP        S59151027 A       8/1984

* cited by examiner

*Primary Examiner* — Kara E Geisel
*Assistant Examiner* — Hina F Ayub
(74) *Attorney, Agent, or Firm* — Banner & Witcoff, Ltd.

(57) ABSTRACT

An ICP emission spectrometer is schematically configured to include an inductively coupled plasma generation unit, a light condensing unit, a spectroscope, a two-dimensional detection unit and a controller. The two-dimensional detection unit includes a CCD image sensor which has multiple pixels laid in a planar shape and detects emission light by causing the emission light emitted from the spectroscope to be imaged on the multiple pixels. Then, the controller determines a pixel used in detecting the emission light among the multiple pixels in accordance with an imaging shape of detection-targeted emission light.

4 Claims, 6 Drawing Sheets

ICP EMISSION SPECTROMETER

This application claims priority from Japanese Patent Application No. 2014-072522 filed on Mar. 31, 2014, the entire subject-matter of which is incorporated herein by reference.

BACKGROUND

1. Technical Field

The disclosure relates to an Inductively Coupled Plasma (ICP) emission spectrometer for analyzing elements (for example, trace impurity elements) contained in a solution sample.

2. Description of the Related Art

An ICP emission spectrometer atomizes or ionizes a solution sample for ICP emission spectroscopy by using inductively coupled plasma (ICP), and performs a spectroscopy analysis on atomic emission lines (spectral lines) emitted at that time so as to perform a quantitative analysis and a qualitative analysis on trace impurity elements. Then, a spectroscope used for the ICP emission spectrometer includes a sequential-type spectroscope which sequentially detects diffracted light of each wavelength and a multi-type spectroscope which simultaneously detects the diffracted light. An ICP emission spectrometer is known which can control a desired wavelength to be located at a position where the desired wavelength is incident on a detector, by driving a diffraction grating using the sequential-type spectroscope (refer to JP-A-S59-151027).

Figure 5:
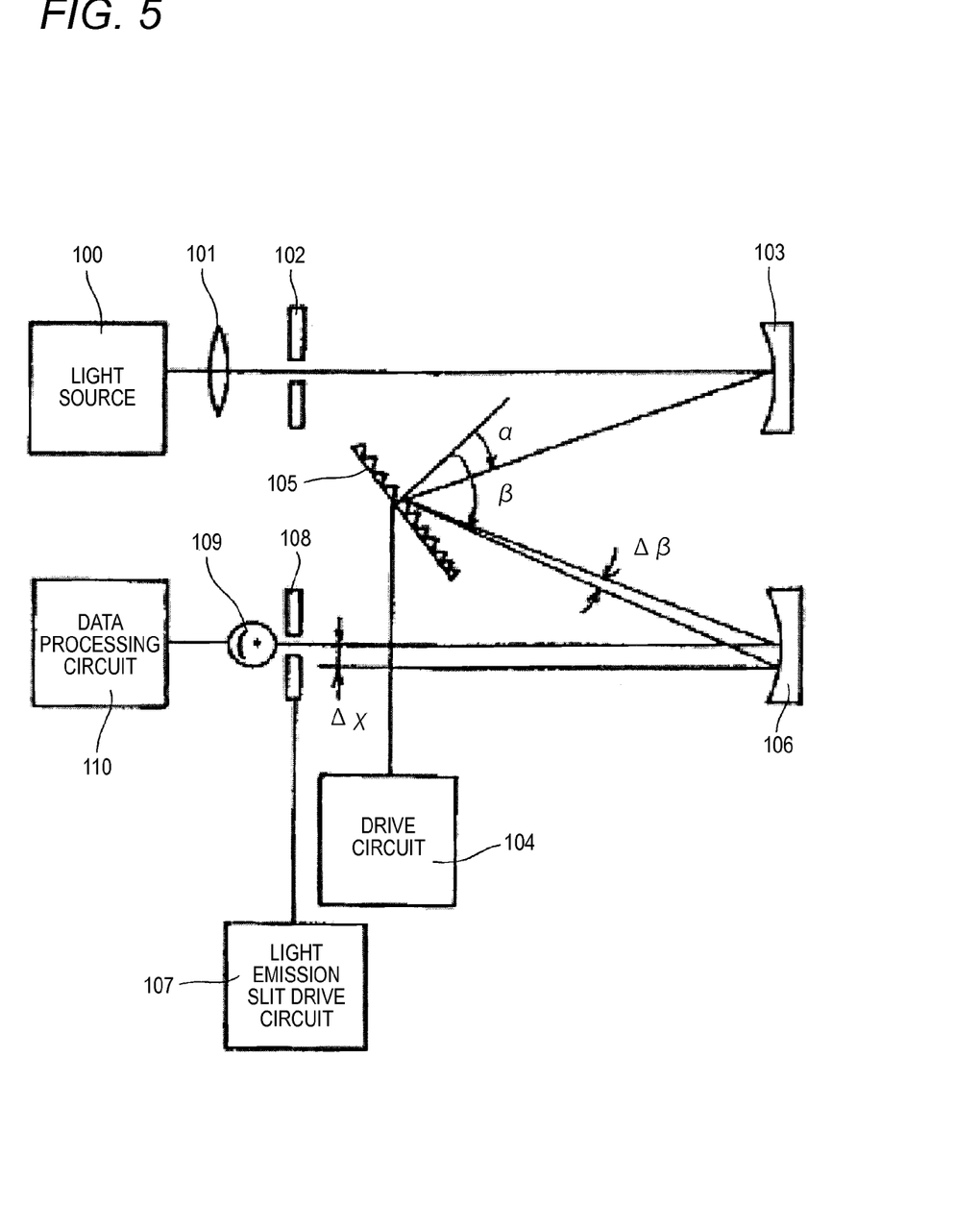
FIG. 5 is a schematic diagram illustrating a configuration of an ICP emission spectrometer according to the related art.

JP-A-S59-151027 illustrated in FIG. 5 discloses a sequential determination emission spectrometer in which light emitted from a light source 100 for emitting the light by exciting a sample is imaged by using a light condensing lens 101, the light transmitted through a light incident slit 102 is introduced into a grating 105 driven by a grating drive circuit 104 by using a collimator 103, the light diffracted by the grating 105 is imaged on a light emission slit 108 driven by a light emission slit drive circuit 107 by suing a camera mirror 106, the light received from the light emission slit 108 is converted into a current by using a detector 109, and an output current is converted into concentration by using a data processing circuit 110. According to this configuration, light intensity is not changed regardless of a position of the light emission slit 108, and there is no change in a refractive index depending on the wavelength. Accordingly, JP-A-S59-151027 discloses that excellent resolution is obtained since the light is exactly imaged on the light emission slit 108 by using the camera mirror 106.

SUMMARY

Figure 6A:
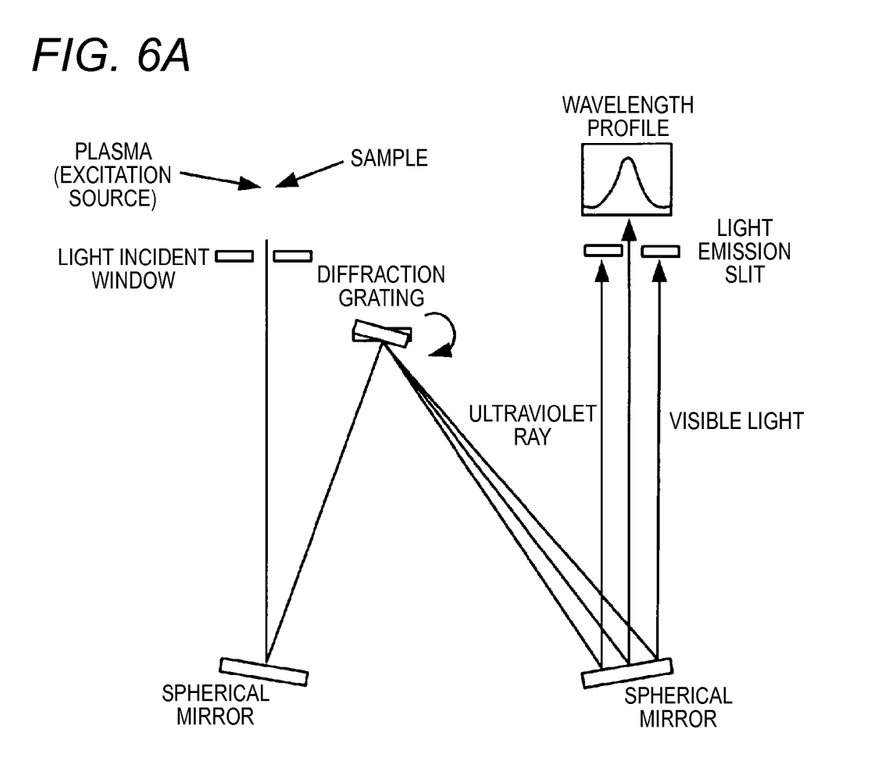
FIG. 6A is a schematic diagram illustrating a spectroscope in the ICP emission spectrometer in the related art.

According to JP-A-S59-151027, the light emission slit 108 is allowed to move. However, the light emission slit 108 has a thin flat plate structure having a fixed hole, and light passing through the hole is detected when the light reaches the detector 109. Incidentally, in a case of an ideal spectroscope having no aberration as illustrated in FIG. 6A, an image having the same shape as the hole shape of a light incident slit is formed at a light emission position, an element is identified using a detected wavelength indicated by a wavelength profile, and element concentration is calculated by using intensity. However, in a case of an actual spectroscope, it is not possible to eliminate factors such as spherical aberration and coma aberration. As a result, it is not possible to form an image corresponding to a shape of the incident light.

Figure 6B:
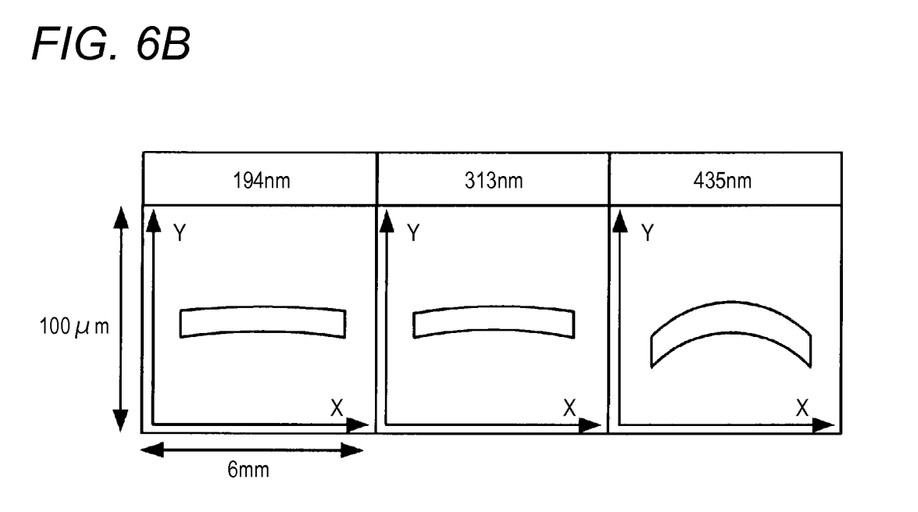
FIG. 6B is a schematic diagram illustrating simulated images on a light emission slit by using a wavelength difference.

That is, as shown on an image formed on the light emission slit when the light incident slit of 10 μm×4 mm illustrated in FIG. 6B is used, the influence caused by the aberration varies depending on an angle of a diffraction grating, thereby causing an imaging shape to vary for each wavelength (for example, 194 nm, 313 nm, and 435 nm) (analysis result of optical simulation). When the diffraction grating is rotated, the image is moved in the Y-axis direction in FIG. 6B. It can be understood that the wavelength which can be simultaneously detected if the position of the light emission slit is fixed, varies and the image is further distorted as the wavelength becomes longer. Consequently, some of the light may not pass through the hole of the light emission slit, thereby impairing measurement intensity in some cases. Furthermore, if the hole of the light emission slit is increased so as not to impair the intensity, fine wavelength separation is not available (degraded wavelength resolution). In addition, after a peak top is measured in the light emission slit, a background position is measured by minutely moving the slit. Consequently, this results in deviation of the measurement time, thereby causing a problem in that it is not possible to correct the influence of fluctuations in plasma light.

Therefore, the present disclosure provides an ICP emission spectrometer which can obtain a measurement result having excellent wavelength resolution without impairing intensity, by using a two-dimensional detection unit and by changing a pixel used for the two-dimensional detection unit in accordance with a wavelength.

According to one aspect of the disclosure, an ICP emission spectrometer comprises: an inductively coupled plasma generation unit configured to obtain atomic emission lines by atomizing or ionizing an analysis-targeted element using inductively coupled plasma; a spectroscope configured to diffract and detect the atomic emission lines; a two-dimensional detection unit having multiple pixels laid in a planar shape and configured to detect emission light by causing the emission light emitted from the spectroscope to be imaged on the multiple pixels; and a controller configured to determine a pixel used in detecting the emission light among the multiple pixels in accordance with an imaging shape of the emission light as a detection target.

The controller may be configured to measure background intensity, based on detection intensity of non-used pixels whose number is the same as the number of pixels used in detecting the emission light.

The two-dimensional detection unit may comprise an image sensor having a detection surface, on which the multiple pixels are formed, and configured to detect the emission light emitted from the spectroscope and imaged on the detection surface, and from among the multiple pixels, a pixel at a position which conforms to the imaging shape of the emission light imaged on the detection surface may be determined as the pixel used in detecting the emission light.

The spectroscope may comprise a diffraction grating, and the controller may be configured to drive the diffraction grating to move the imaging shape of the emission light imaged on the detection surface so as to obtain wavelength profile of the emission light.

When a position of the imaging shape of the emission light on the detection surface overlaps with a position of an estimated shape on predetermined pixels of the multiple pixels, the estimated shape having been determined by a prior analysis or a prior measurement while driving the diffraction grating to move the imaging shape of the emission light, the controller may be configured to determine an overlapping position of the imaging shape of the emission light and the estimated shape as a peak top position of the wavelength profile.

According to the present disclosure, in accordance with a wavelength of detection-targeted emission light by using a two-dimensional detection unit, a pixel used in detecting the emission light is determined among multiple pixels. Therefore, there is no possibility that wavelength resolution may be impaired. In addition, it is possible to detect the emission light without impairing imaging light of the emission light emitted from a spectroscope. In addition, it is possible to provide an ICP emission spectrometer which can perform more accurate measurement by means of simultaneous background correction.

DETAILED DESCRIPTION

Hereinafter, a preferred embodiment of an ICP emission spectrometer according to the present disclosure will be described in detail with reference to FIGS. 1 to 4F.

Figure 1:
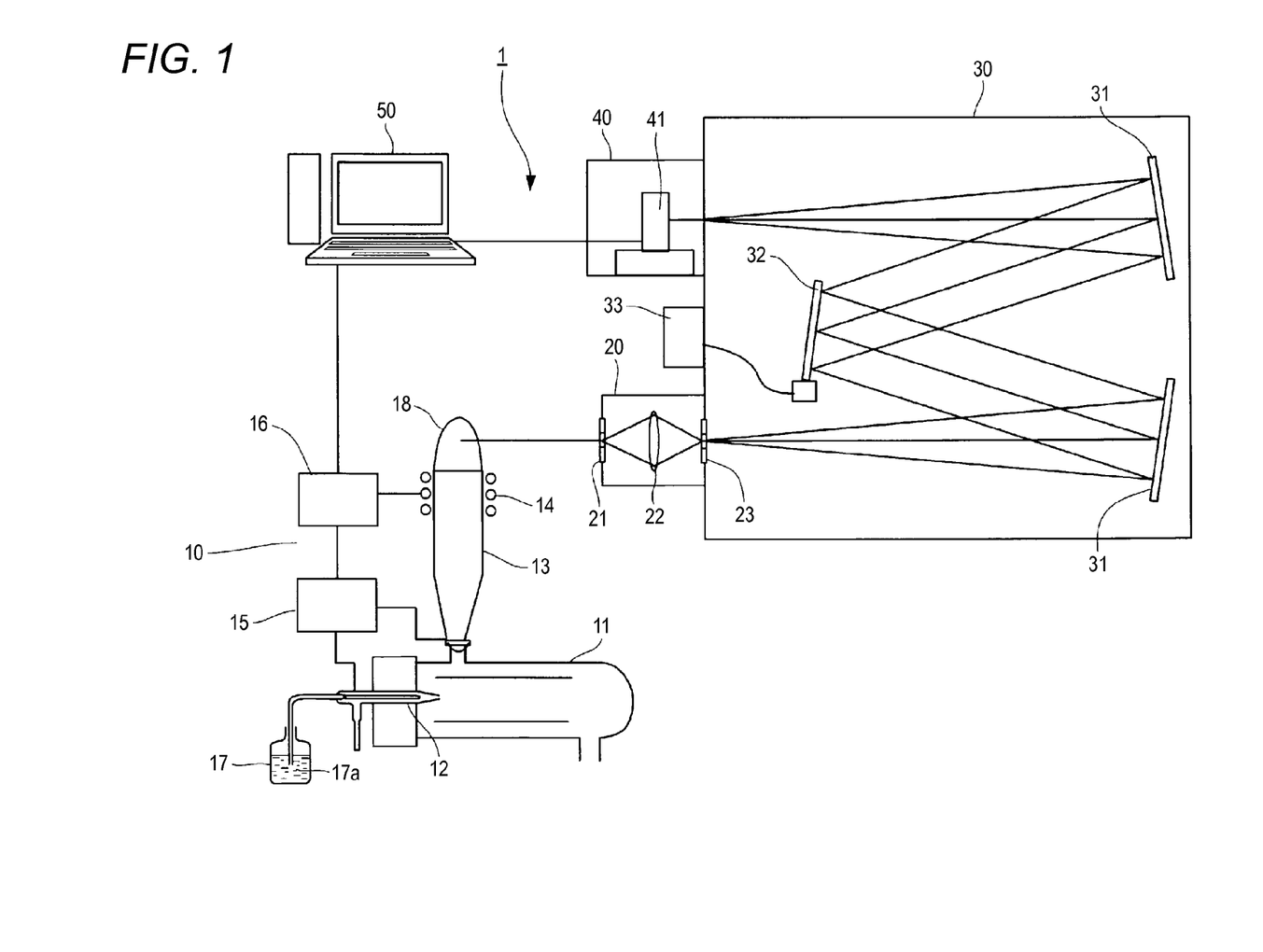
FIG. 1 is a conceptual diagram illustrating an example of an ICP emission spectrometer according to the present disclosure.

FIG. 1 is a conceptual diagram illustrating an example of the ICP emission spectrometer according to the present disclosure.

An ICP emission spectrometer 1 is schematically configured to include an inductively coupled plasma generation unit 10, a light condensing unit 20, a spectroscope 30, a two-dimensional detection unit 40, and a controller 50. The inductively coupled plasma generation unit 10 is schematically configured to include a spray chamber 11, a nebulizer 12, a plasma torch 13, a high frequency coil 14, a gas controller 15, and a high frequency power source 16.

The light condensing unit 20 for condensing atomic emission lines is arranged between the inductively coupled plasma generation unit 10 and the spectroscope 30, and includes a light incident window 21, a light condensing lens 22, and a light incident slit 23. The spectroscope 30 for diffracting and detecting the atomic emission lines includes multiple spherical mirrors 31, a diffraction grating 32, and a drive unit 33 for driving the diffraction grating 32. For example, a driving method is a sine bar method or a DD motor method. Driving is performed by the drive unit 33 being directly coupled to the diffraction grating 32.

The two-dimensional detection unit 40 is a two-dimensional detector including a CCD image sensor 41. The CCD image sensor 41 has multiple pixels laid in a planar shape. The two-dimensional detection unit 40 detects emission light by causing the emission light of atomic emission lines emitted from the spectroscope 30 to be imaged on the multiple pixels. In the above description, the diffraction grating 32 is operated, but the two-dimensional detection unit 40 may be operated.

The controller 50 is a computer or the like, and controls the overall ICP emission spectrometer 1 so as to determine a pixel used in detecting the emission light within the multiple pixels of the CCD image sensor 41 in accordance with the wavelength of the emission light of detection-targeted atomic emission lines. In addition, the controller 50 measures background intensity, based on detection intensity of non-used pixels whose number is the same as the number of pixels used in detecting the emission light.

Figure 2:
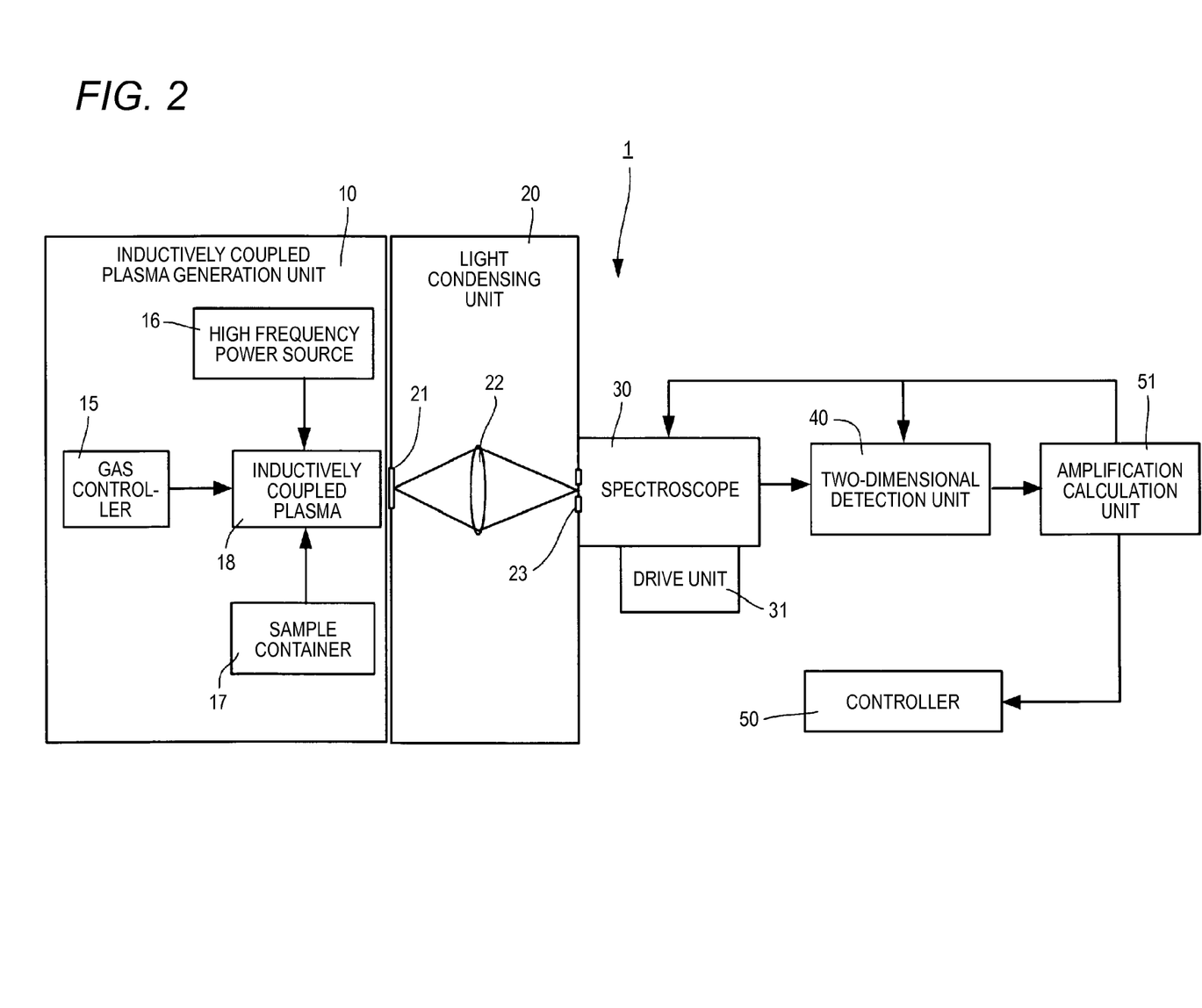
FIG. 2 is a block diagram illustrating an example of the ICP emission spectrometer according to the present disclosure.

FIG. 2 is a block diagram illustrating an example of the ICP emission spectrometer according to the present disclosure.

Argon gas serving as plasma gas is controlled by the gas controller 15 so as to be introduced into the plasma torch 13. Then, a high frequency current is caused to flow into the high frequency coil 14 from the high frequency power source 16, thereby causing the argon gas to generate an inductively coupled plasma 18 (hereinafter, referred to as a plasma) above the plasma torch 13.

On the other hand, the argon gas serving as carrier gas which is supplied into the nebulizer 12 is ejected from a distal end of the nebulizer 12 into the spray chamber 11, and negative pressure suction of the argon gas sucks up a solution sample 17a of a sample container 17, thereby ejecting the solution sample 17a from the distal end of the nebulizer 12. The ejected solution sample 17a is allowed to have uniformized particles and stabilized air flows inside the spray chamber 11, and is controlled by the gas controller 15 so as to be introduced into the plasma torch 13. Then, sample molecules (or atoms) of the solution sample 17a are heated and excited in the plasma 18 so as to emit light.

The solution sample 17a is a standard sample whose concentration of contained elements is known and which is used in creating a calibration curve, or an unknown sample whose concentration a user wants to know. Replacement of the solution sample 17a into the sample container 17 can be performed manually or automatically by using an automatic sampler or the like.

The atomic emission lines in which an analysis-targeted element of the solution sample 17a is atomized or ionized by the plasma 18 are incident on the light condensing unit 20 for condensing the atomic emission lines, and pass through the light incident slit 21 and the light condensing lens 22. After passing through the light incident slit 23, the atomic emission lines are incident on the inside of the spectroscope 30.

The atomic emission lines received through the light incident slit 23 are diffracted and detected by the spherical mirror 31 and the diffraction grating 32 inside the spectroscope 30, and are incident on the two-dimensional detection unit 40. The two-dimensional detection unit 40 detects the emission light by using multiple pixels laid in a planar shape in the CCD image sensor 41 and causing the emission light of the atomic emission lines to be imaged on the multiple pixels.

The multiple pixels laid in the planar shape in the CCD image sensor 41 serve as a detection surface on which micro-light-receiving elements (photodiodes) formed of semiconductor chips are arrayed two-dimensionally. Each pixel generates and outputs a signal (pixel signal) corresponding to intensity of the received light. The pixel signal is transmitted to the controller 50. The controller 50 creates an emission spectrum having a predetermined wavelength, identifies an element from a peak wavelength which appears in the spectrum, and performs a quantitative analysis based on peak intensity.

The emission light of the detected atomic emission lines is analyzed and subjected to data processing by the controller 50. A qualitative analysis is performed on an analysis-targeted element (for example, trace impurity element) contained in the solution sample 17a, based on the wavelength of the atomic emission lines (spectral line), and a quantitative analysis is performed on the element, based on the intensity of the atomic emission lines (spectral line). The atomic emission lines passing through the spectroscope 30 and the two-dimensional detection unit 40 are amplified by an amplification calculation unit 51, and are recorded as measurement data in the controller 50. The amplification calculation unit 51 performs wavelength-swept control for the spectroscope 30, and performs control of a detector voltage or integration time for the two-dimensional detection unit 40.

FIGS. 3A to 4F are schematic views illustrating an obtaining sequence of a wavelength profile by using a two-dimensional detection unit.

In the embodiment, the drawings illustrate a detection surface 41a of the CCD image sensor 41 in which 30 pixels are respectively arrayed in the horizontal and vertical directions, an analysis image formation (imaging shape of the emission light) S of the light having a specific wavelength at a peak top position which is obtained on the detection surface 41a, an estimated shape T on predetermined pixels, and a background shape BG. FIGS. 3A to 3F illustrate an example of the analysis image formation S of light having a wavelength of 194 nm, and FIGS. 4A to 4F illustrate an example the analysis image formation S of light having a wavelength of 435 nm. Depending on a wavelength range, a shape of the analysis image formation S on the detection surface 41a varies. Depending on an aberration of an optical system, some wavelengths may have a bow-shaped image (refer to FIGS. 4A to 4F).

Figure 3A:
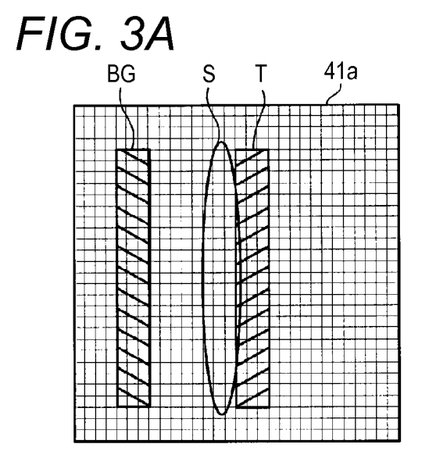
FIGS. 3A to 3F are schematic views illustrating an obtaining sequence of a wavelength profile having a wavelength of 194 nm by using a two-dimensional detection unit of the ICP emission spectrometer according to the present disclosure.
Figure 3B:
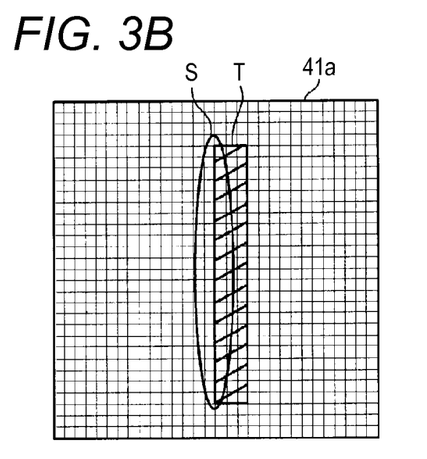
Figure 3C:
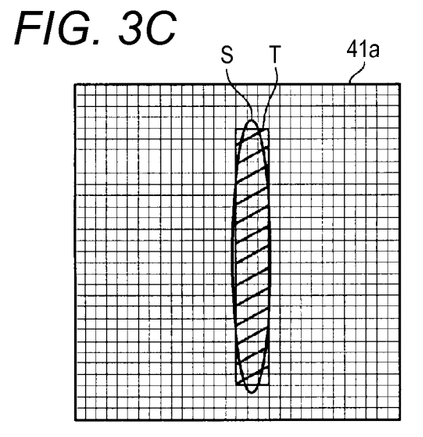
Figure 3D:
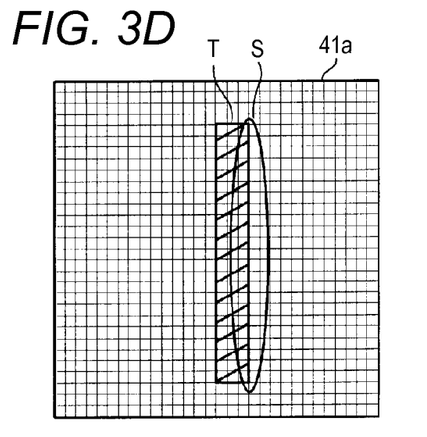
Figure 3E:
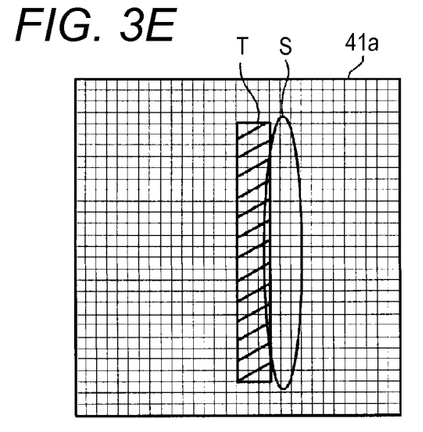
Figure 3F:
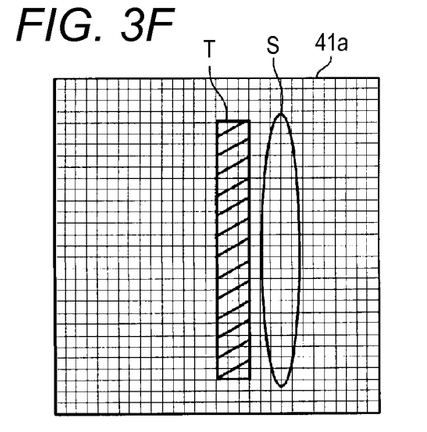
Figure 4A:
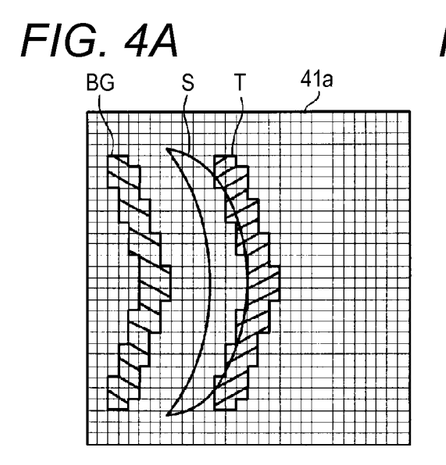
FIGS. 4A to 4F are schematic views illustrating an obtaining sequence of the wavelength profile having a wavelength of 435 nm by using the two-dimensional detection unit of the ICP emission spectrometer according to the present disclosure.
Figure 4B:
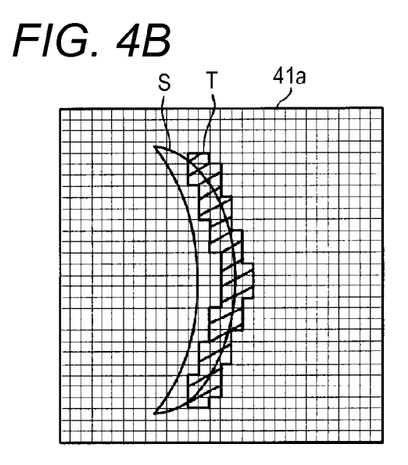
Figure 4C:
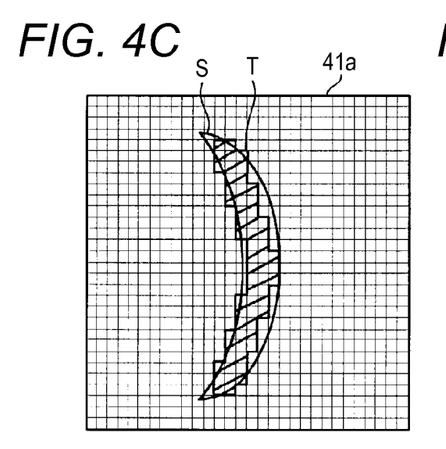
Figure 4D:
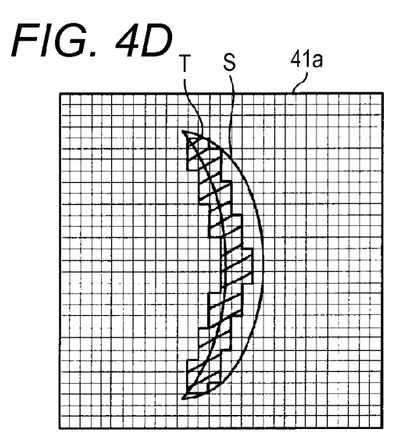
Figure 4E:
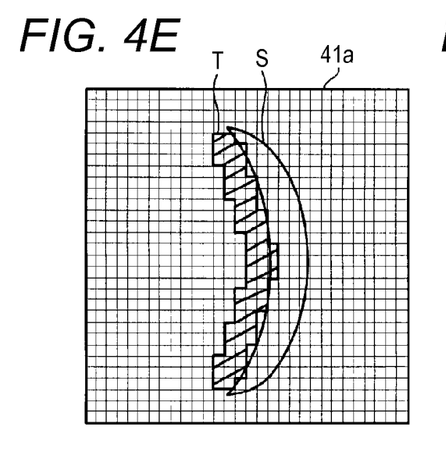
Figure 4F:
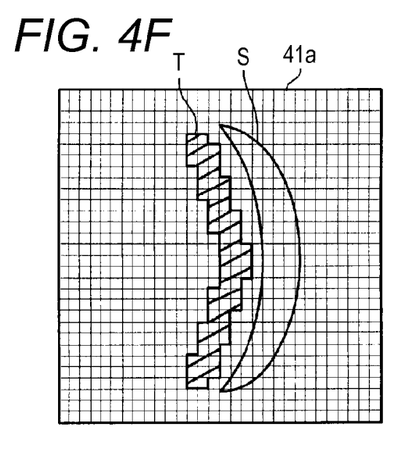

Then, the drawings illustrate a state where the diffraction grating 32 is driven and the analysis image formation S is moved from FIGS. 3A and 4A to FIGS. 3F and 4F so as to obtain wavelength profile data. In addition, FIGS. 3C and 4C illustrate that the analysis image formation S and the estimated shape T overlap each other. That is, at the time when both of these overlap each other, the measurement is performed by regarding the overlapping position as the peak top position of the wavelength profile, thereby performing the quantitative measurement at the specific wavelength position. When the two-dimensional detection unit 40 is operated, a shape and the number of pixels in use are shifted to the right and left without any changes.

Only pixels at positions which conform to the shape of the analysis image formation S at a light emission position of each diffracted wavelength at the spectroscope 30 are used to obtain actual intensity. Then, the controller 50 determines the pixel to be used in detecting the emission light among the multiple pixels on the detection surface 41a, in accordance with the detection-targeted emission light. That is, the controller 50 determines the pixel to be exposed so as to follow the shape of the image formed similarly to the estimated shape T, and does not cause other pixels to be exposed. Therefore, as compared to a strip-type light emission slit in the related art, the intensity is not low, and a shape of the wavelength profile becomes clear.

When the pixel used in each wavelength is determined, the estimated shape T of the light which is determined by a prior analysis of the spectroscope 30 is utilized. However, it is also possible to determine the pixel based on intensity distribution information by performing prior measurement on all pixels on the detection surface 41a before actual measurement.

The movement (FIGS. 3A to 3F and FIGS. 4A to 4F) of the analysis image formation S on the detection surface 41a is performed by driving the diffraction grating 32. However, the detection surface 41a may be moved by driving the two-dimensional detection unit 40. The resolution of the movement distance may be minute. It is possible to obtain a higher resolution wavelength profile shape by measuring the minute movement. It is also possible to obtain the intensity for the fixed time by stopping the two-dimensional detection unit 40 during the quantitative analysis. It is also possible to measure the intensity by stopping the analysis image formation S without allowing the minute movement of the analysis image formation S. However, the higher resolution wavelength profile is likely to be obtained when the analysis image formation S is moved.

Furthermore, if the intensity of the background shape BG is measured during the quantitative analysis, it is possible to perform simultaneous background measurement which is unavailable in the related art. The intensity of the background shape BG which has the same shape as the pixel in use at the peak top position and is located at a slightly deviated position is measured simultaneously. That is, the controller 50 can measure background intensity, based on detection intensity of non-used pixels whose number is the same as the number of pixels having the estimated shape T which are used in detecting the emission light. Since background correction can be performed simultaneously, it is possible to perform more accurate measurement.

In the background measurement, all pixels are exposed and any desired pixel is selected. In this manner, it is possible to perform the simultaneous background measurement at any desired position. In addition, if it is important to obtain accurate intensity of a specific wavelength, the number of pixels within the same area may be reduced. If it is important to obtain the intensity, the pixels may be increased in reverse. Then, since the two-dimensional detection unit 40 is used, the light emission slit or photomultiplier in the related art may be excluded.

Without being limited to the above-described embodiment, the present disclosure can be appropriately modified or improved. In addition, materials, shapes, dimensions, numerical values forms, the number, arrangement locations, or the like of the respective configuration elements in the above-described embodiment are optionally selected and not limited as long as the present disclosure can be achieved. For example, in the present embodiment, the light condensing unit 20 is disposed, but the light condensing lens 22 or the light incident slit 23 is not essential. In addition, a mirror may be used in place of the light condensing lens 22.

An ICP emission spectrometer according to the present disclosure can perform more accurate optical detection as compared to an ICP emission spectrometer in the related art, and thus is industrially applicable.

What is claimed is:

1. An ICP emission spectrometer comprising:
an inductively coupled plasma generation unit configured to obtain atomic emission lines by atomizing or ionizing an analysis-targeted element using inductively coupled plasma;
a spectroscope configured to diffract and detect the atomic emission lines, wherein the spectroscope comprises a diffraction grating;
a two-dimensional detection unit having multiple pixels laid in a planar shape and configured to detect emission light by causing the emission light emitted from the spectroscope to be imaged on the multiple pixels; and
a controller configured to determine a pixel used in detecting the emission light among the multiple pixels in accordance with an imaging shape of the emission light as a detection target,
wherein the two-dimensional detection unit comprises an image sensor having a detection surface, on which the multiple pixels are formed, and is configured to detect the emission light emitted from the spectroscope and imaged on the detection surface,
wherein from among the multiple pixels, a pixel at a position which conforms to the imaging shape of the emission light imaged on the detection surface is determined as the pixel used in detecting the emission light, and
wherein the controller is configured to drive the diffraction grating to move the imaging shape of the emission light imaged on the detection surface and to determine a pixel of the multiple pixels to be exposed so as to follow the imaging shape of the emission light to obtain a wavelength profile of the emission light.

2. The ICP emission spectrometer according to claim 1, wherein the controller is configured to measure background intensity, based on a detection intensity of non-used pixels, wherein the number of non-used pixels is the same as the number of pixels used in detecting the emission light.

3. An ICP emission spectrometer comprising:
an inductively coupled plasma generation unit configured to obtain atomic emission lines by atomizing or ionizing an analysis-targeted element using inductively coupled plasma;
a spectroscope configured to diffract and detect the atomic emission lines;
a two-dimensional detection unit having multiple pixels laid in a planar shape and configured to detect emission light by causing the emission light emitted from the spectroscope to be imaged on the multiple pixels; and
a controller configured to:
determine a pixel used in detecting the emission light among the multiple pixels in accordance with an imaging shape of the emission light as a detection target; and
measure background intensity based on detection intensity of non-used pixels, wherein a number of non-used pixels is the same as a number of pixels used in detecting the emission light,
wherein the two-dimensional detection unit comprises an image sensor having a detection surface, on which the multiple pixels are formed, and configured to detect the emission light emitted from the spectroscope and imaged on the detection surface,
wherein from among the multiple pixels, a pixel at a position which conforms to the imaging shape of the emission light imaged on the detection surface is determined as the pixel used in detecting the emission light,
wherein the spectroscope comprises a diffraction grating,
wherein the controller is configured to drive the diffraction grating to move the imaging shape of the emission light imaged on the detection surface so as to obtain a wavelength profile of the emission light, and
wherein when a position of the imaging shape of the emission light on the detection surface overlaps with a position of an estimated shape on predetermined pixels of the multiple pixels while driving the diffraction grating to move the imaging shape of the emission light, the estimated shape having been determined by a prior analysis or a prior measurement, the controller is configured to determine an overlapping position of the imaging shape of the emission light and the estimated shape as a peak top position of the wavelength profile.

4. An ICP emission spectrometer comprising:
an inductively coupled plasma generation unit configured to obtain atomic emission lines by atomizing or ionizing an analysis-targeted element using inductively coupled plasma;
a spectroscope comprising a diffraction grating, wherein the spectroscope is configured to diffract and detect the atomic emission lines;
a two-dimensional detection unit comprising an image sensor having a detection surface on which multiple pixels are laid in a planar shape, wherein the two-dimensional detection unit is configured to detect emission light by causing the emission light emitted from the spectroscope to be imaged on the multiple pixels;
a controller configured to:
determine a pixel used in detecting the emission light from among the multiple pixels at a position which conforms to an imaging shape of the emission light on the detection surface;
drive the diffraction grating to move the imaging shape of the emission light imaged on the detection surface so as to obtain a wavelength profile of the emission light,
wherein when a position of the imaging shape of the emission light on the detection surface overlaps with a position of an estimated shape on predetermined pixels of the multiple pixels while driving the diffraction grating to move the imaging shape of the emission light, the estimated shape having been determined by a prior analysis or a prior measurement, the controller is configured to determine an overlapping position of the imaging shape of the emission light and the estimated shape as a peak top position of the wavelength profile.

* * * * *